(12) United States Patent
Kobayashi et al.

(10) Patent No.: US 7,323,603 B2
(45) Date of Patent: Jan. 29, 2008

(54) METHOD FOR ALDOL REACTION IN WATER

(75) Inventors: Shu Kobayashi, Tokyo (JP); Kei Manabe, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 881 days.

(21) Appl. No.: 10/471,693

(22) PCT Filed: Mar. 8, 2002

(86) PCT No.: PCT/JP02/02185

§ 371 (c)(1),
(2), (4) Date: Feb. 23, 2004

(87) PCT Pub. No.: WO02/074724

PCT Pub. Date: Sep. 26, 2002

(65) Prior Publication Data

US 2004/0133044 A1 Jul. 8, 2004

(30) Foreign Application Priority Data

Mar. 15, 2001 (JP) .............................. 2001-075091

(51) Int. Cl.
*C07C 45/00* (2006.01)
(52) U.S. Cl. ...................... 568/312; 568/315; 568/388; 568/391

(58) Field of Classification Search ..................... None
See application file for complete search history.

(56) References Cited

FOREIGN PATENT DOCUMENTS

| JP | 7-25808 | 1/1995 |
|---|---|---|
| JP | 11-12216 | 1/1999 |
| JP | 11-244705 | 9/1999 |
| WO | 00/7719 | 2/2000 |

OTHER PUBLICATIONS

Y. Mori et al., "Catalytic Use of a Boron Source for Boron Enolate Mediated Stereoselective Aldol Reactions in Water", Angew. Chem. Int. Ed. 2001, vol. 40, No. 15, pp. 2816-2818.
K. Ishihara et al., "Diarylborinic Acids as Efficient Catalysts for Selective Dehydration of Aldols" Synlett 1997, No. 5, pp. 597-599.

*Primary Examiner*—Sikarl A. Witherspoon
(74) *Attorney, Agent, or Firm*—Wenderoth, Lind & Ponack, L.L.P.

(57) ABSTRACT

A method for aldol reaction in water, which comprises: reacting an aldehyde with a silyl enol ether in an aqueous medium in the presence of a boronic acid represented by the following general formula (1):

$$R^1R^2BOH \qquad (1)$$

(wherein $R^1$ and $R^2$ are the same or different hydrocarbon groups that may contain a substituent), a surfactant, and a Brønsted acid is provided. This method for aldol reaction in water uses a catalytic amount of the boron source to give products in high yield and selectivity.

9 Claims, 1 Drawing Sheet

METHOD FOR ALDOL REACTION IN WATER

This application is the national stage of PCT/JP02/02185 filed Mar. 8, 2002 and published as WO 02/074724 on Sep. 26, 2002.

TECHNICAL FIELD

The present invention relates to a method for performing aldol reaction in water. The invention more specifically relates to a method for performing aldol reaction that gives high yield and excellent selectivity in an aqueous medium without the use of organic solvents.

BACKGROUND ART

Organic reactions that proceed in aqueous medium without the use of organic solvents have been attracting attention from the viewpoint of environmental care. However, various disadvantages existed for the use of aqueous medium for organic reactions, causing the procedure to be considered difficult. The first main disadvantage is that organic compounds are mostly insoluble in water; the second main disadvantage is that most reaction intermediates and reagents such as catalysts are decomposed by even a trace of water.

The inventors have reported Lewis acid-surfactant-combined catalysts (LASC: e.g., Japanese Patent Application No. 10-53075), which enable various organic synthesis methods such as aldol reaction, allylation reaction, Mannich reaction and Michael reaction in aqueous mediums. Although such Lewis acid-surfactant-combined catalysts is important in that they can give products with relatively high yield and selectivity, higher catalytic activity was desired for aldol reaction in water.

Organic reactions using boron enolates have been well-known as a method for providing products in high selectivity. However, a stoichiometric amount of the boron source was required in previously reported organic reactions using boron enolates, and an organic reaction method using a catalytic amount of boron source that can give the product in high yield and selectivity has not been known.

Accordingly, the present invention has been accomplished in view of the above circumstances, and thus, an object of the invention is to solve the problems of the prior technologies, thereby providing a method for aldol reaction in water, which uses a catalytic amount of boron source and gives the product in high yield and selectivity.

DISCLOSURE OF INVENTION

As a means to solve the above problems, the present invention firstly provides a method for aldol reaction in water, which comprises reacting an aldehyde with a silyl enol ether in an aqueous medium in the presence of a boronic acid represented by the following general formula (1):

$$R^1R^2BOH \qquad (1)$$

(wherein $R^1$ and $R^2$ are the same or different hydrocarbon groups that may contain a substituent), a surfactant, and a Brønsted acid.

Secondly, the present invention provides as embodiments of the method for aldol reaction in water, the use of an anionic surfactant as the surfactant and thirdly, the use of an organic acid as the Brønsted acid.

Furthermore, the present invention fourthly provides the above method for aldol reaction in water, wherein the boronic acid represented by the following general formula (1):

$$R^1R^2BOH \qquad (1)$$

(wherein $R^1$ and $R^2$ are the same or different hydrocarbon groups that may contain a substituent) is bonded to a silyl enolate to form a boron enolate intermediate.

BEST MODE FOR CARRYING OUT THE INVENTION

Figure 1:
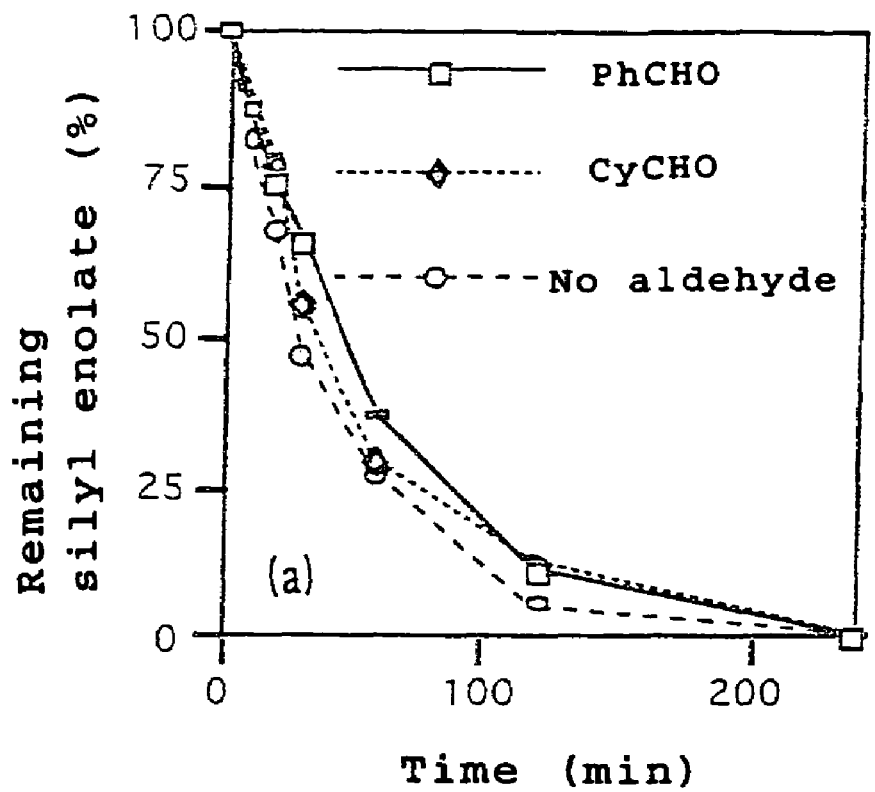
FIG. 1 shows the change in amount of silyl enolate with time in the presence of $Ph_2BOH$, benzoic acid and SDS in the Reference Example of the present invention (a: effect of aldehyde, b: relationship between the concentration and the rate of disappearance of the silyl enolate).
Figure 1:
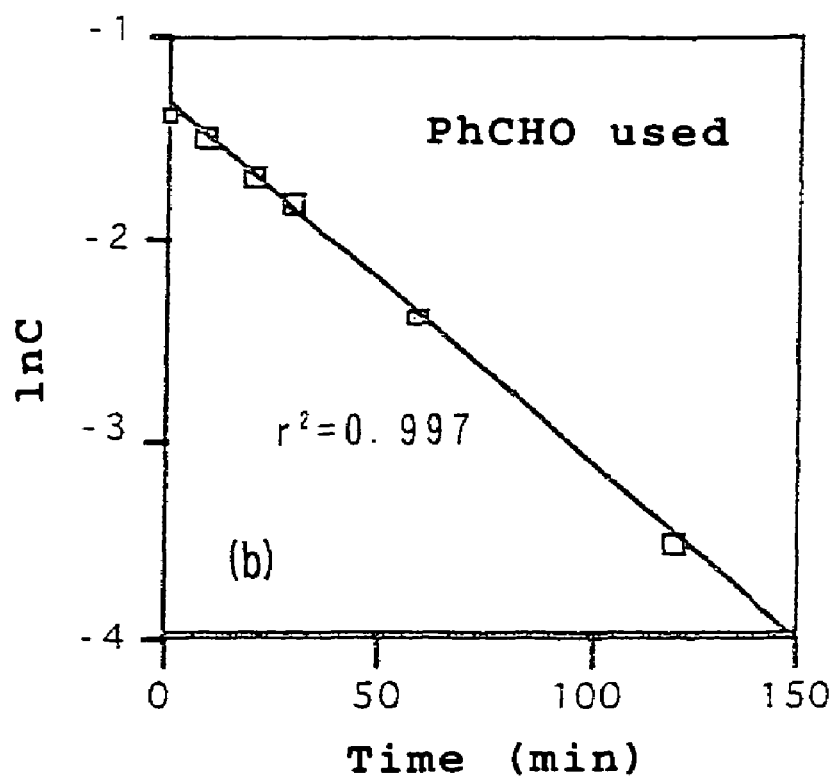

As described above, the present inventors have previously reported catalyst systems that enable organic reactions in water (*Tetrahedron Lett*. 1998, 39, 5389-5392; *J. Am. Chem. Soc.* 1998, 120, 9517-9525; *Synlett* 1999, 547-548; *J. Am. Chem. Soc.* 2000, 122, 7202-7207; etc.) As a result of intense research based on such knowledge, the inventors have found that a boronic acid represented by the following general formula (1):

$$R^1R^2BOH \qquad (1)$$

(wherein $R^1$ and $R^2$ are the same or different hydrocarbon groups that may contain a substituent) can effectively act as a catalyst for aldol reaction in water, and achieved the present invention.

Thus, in the method for aldol reaction in water of the present invention, an aldehyde and a silyl enolate are reacted in the presence of boronic acid represented by the aforementioned general formula (1), a surfactant and a Brønsted acid, whereby the aldol reaction proceeds in high yield and diastereoselectivity even in water without a trace of organic solvent. In the boronic acid represented by the general formula (1), $R^1$ and $R^2$ may be the same or different groups, and may be selected from linear hydrocarbon groups such as methyl, ethyl, propyl and butyl groups, cyclic hydrocarbon groups such as cyclopentyl, cyclohexyl, phenyl and toluyl groups, etc. These hydrocarbon groups may contain various substituents, which may further contain heteroatoms such as N, S and O. Such compounds are generally stable in water; diphenylboronic acid ($Ph_2BOH$), wherein both $R^1$ and $R^2$ are Ph, is most stable in water and is thus preferable.

In the aldol reaction in water of the present invention, the boronic acid of the general formula (1) must coexist with a surfactant and a Brønsted acid to exhibit high catalytic activity, as can be seen clearly from the Examples described hereinafter. The surfactant may be appropriately selected from anionic surfactants such as sodium dodecyl sulfate (SDS) and dodecylbenzenesulfonic acid, neutral surfactants such as Triton X-100, and cationic surfactants such as cetyltrimethylammonium bromide (CTAB). Among them, anionic surfactants are preferable because the surface of the colloidal particles they form have higher proton concentrations and improve the yield and stereoselectivity of the aldol reaction.

In the method for aldol reaction in water of the present invention, further to the boronic acid of general formula (1)

and the surfactant, a Brønsted acid is added which leads the aldol reaction to proceed with high yield and stereoselectivity.

It has been reported that the strength of the group that is liberated from the boron atom is important in silicon-boron exchange reactions (*Chem. Lett.* 1981, 153-156). Hence, in the reaction between the boronic acid of general formula (1) and the silyl enolate, by adding a Brønsted acid, it may be presumed that the hydroxyl group attached to the boron atom is protonated, thereby accelerating the elimination of the hydroxyl group.

Therefore, in the present invention, the Brønsted acid is not limited as long as it can donate a proton, and may be selected from various inorganic acids and organic acids. Preferably, it is an organic acid, particularly, benzoic acid, acetic acid, etc., which provides the reaction product in high selectivity and yield.

In the method for aldol reaction in water of the present invention, the solvent may be water and there is no need to add any organic solvent. The reaction temperature and the reaction time are not particularly restricted. The aldol reaction of the present method proceeds sufficiently even at low temperatures of, for example, 0 to 50° C.; the reaction time may be selected in accordance with the reaction temperature, the amount of catalyst, etc., but 1 to 30 hour gives the product in high yield and selectivity.

Hereinafter, embodiments of the invention will be described in more detail by the following Examples with reference to the attached drawings. Of course, the invention is not restricted to these Examples and various embodiments may be considered.

EXAMPLES

Example 1

Aldol Reaction in Water Using Diphenylboronic Acid

Using diphenylboronic acid ($Ph_2BOH$: Compound 1) synthesized by a known method (*Chem. Lett.* 1982, 241-244) as a catalyst, and using sodium dodecyl sulfate (SDS) as a surfactant, the aldol reaction of benzaldehyde and silyl enol ether (Compound 2), was performed in water in accordance with the following chemical formula (A):

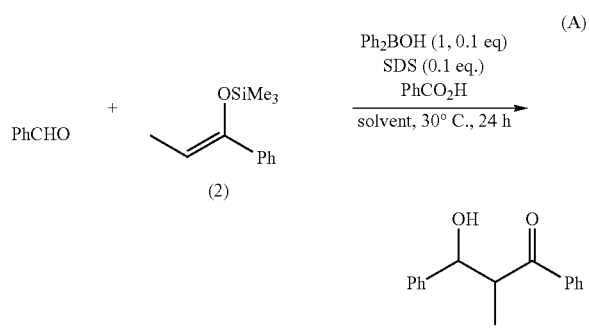

$Ph_2BOH$ (0.025 mmol), benzoic acid (0.0025 mmol), and SDS (0.025 mmol) were added to water (1.5 mL) and stirred to obtain a white dispersion, after which the aldehyde (0.25 mmol) and the silyl enolate (0.375 mmol) were successively added thereto at 30° C. After 24 hours, a saturated $NaHCO_3$ solution and brine were added to the reaction mixture, and the mixture was extracted with ethyl acetate dried over $Na_2SO_4$, and concentrated. The aldol product thus obtained was purified by TLC ($SiO_2$, ethyl acetate/hexane=1/3).

Conditions for the syntheses, yields and stereoslectivities are shown in Table 1.

TABLE 1

| Reaction No. | Solvent | $PhCO_2H$ (eq.) | Yield (%) | syn/anti |
|---|---|---|---|---|
| 1 | $H_2O$ | — | trace | — |
| 2 | $H_2O$ | 0.01 | 90 | 92/8 |
| 3[b] | $H_2O$ | — | 2 | 53/47 |
| 4[b] | $H_2O$ | 0.01 | 27 | 58/42 |
| 5[c] | $H_2O$ | 0.01 | 4 | 91/9 |
| 6[d] | $H_2O$ | 0.01 | 93 | 94/6 |
| 7 | $Et_2O$ | 0.01 | trace | — |
| 8 | $CH_2Cl_2$ | 0.01 | trace | — |
| 9 | — | 0.01 | 24 | 90/10 |

[b]: Without Compound (1), [c]: Without SDS, [d]: 0° C.

The reaction proceeded very slowly in the presence of 0.1 eq. of $Ph_2BOH$ and SDS (Reaction No. 1). However, the yield increased remarkably by the addition of benzoic acid (reaction No. 2). Further, the product obtained was higher in the diastereoselectivity (syn/anti) than the products obtained using the LASC system previously reported by the inventors (e.g., *Tetrahedron Lett.* 1998, 39, 5389-5392; *J. Am. Chem. Soc.* 2000, 122, 7202-7207).

In the system using only SDS without adding $Ph_2BOH$ and benzoic acid (Reaction No. 3) and the system using only SDS and benzoic acid without adding $Ph_2BOH$ (Reaction No. 4), the products showed low yield and diastereoselectivity. On the other hand, in the system using only $Ph_2BOH$ and benzoic acid without adding SDS (Reaction No. 5), although high syn selectivity was obtained, the yield was extremely low.

Thus, it was confirmed that by reacting benzaldehyde and silyl enol ether at low temperature (0° C.) in the presence of $Ph_2BOH$, SDS and benzoic acid (Reaction No. 6), the product can be obtained in high yield and selectivity, even in water.

Further, in the systems where organic solvents were used instead of water (Reaction Nos. 7 and 8), the aldol reactions hardly proceeded, and in the system where no solvent was used (Reaction No. 9), the yield obtained was lower than that obtained by the system where water was used. These results suggested that it is important to perform the aldol reaction which uses $Ph_2BOH$ as the catalyst in the presence of water.

Example 2

Effect of the Surfactant

The Aldol reaction of Example 1 was performed using various surfactants in accordance with the following chemical formula (B):

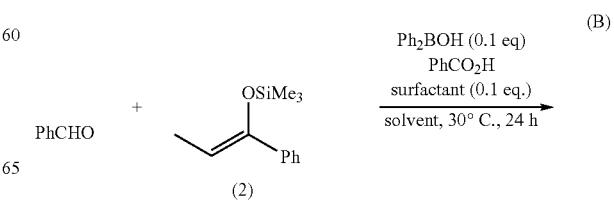

-continued

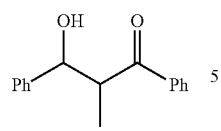

Z/E=>99/<1

The results are shown in Table 2.

TABLE 2

| Reaction No. | Surfactant | Solvent | Yield (%) | syn/anti |
|---|---|---|---|---|
| 1 | SDS | $H_2O$ | 90 | 92/8 |
| 2 | $NaO_3SC_6H_4C_{12}H_{25}$ | $H_2O$ | 81 | 93/7 |
| 3 | TritonX-100 | $H_2O$ | trace | — |
| 4 | CTAB | $H_2O$ | 8 | 87/13 |
| 5 | — | $H_2O$ | 4 | 91/9 |
| 6 | — | $H_2O$/THF (1/9) | trace | — |
| 7 | — | $H_2O$/EtOH (1/9) | 13 | 73/27 | when the anionic surfactants SDS and dodecylbenzene sulfonate were used, excellent yields and stereoselectivities were obtained (Reaction Nos. 1 and 2). On the other hand, when TritonX-100 known as a polyoxyethylene ether-type neutral surfactant (Reaction No. 3) and the cationic surfactant cetyltrimethylammonium bromide (CTAB: Reaction No. 4) were used, the reaction hardly proceeded. These results suggested that the aldol reaction proceed in high yield and stereoselectivity when an anionic surfactant coexists in the reaction system.

This effect of the anionic surfactant may be caused by the electrostatic interaction between the proton and the anionic surfactant; that is, the concentration of proton existing on the surface of the colloidal particles formed by SDS is higher than for those formed by TritonX-100 and CTAB.

Further, the reaction hardly proceeded when $H_2O$/EtOH or $H_2O$/THF (Reaction Nos. 6 and 7) were used. Thus, it was shown that the addition of a surfactant is required in the aldol reaction using $Ph_2BOH$.

Example 3

Effect of Brønsted Acid

The Aldol reaction of the above chemical formula (B) was carried out using SDS as the surfactant and various Brønsted acids.
The results are shown in Table 3.

TABLE 3

| Reaction No. | Bronsted acid | Reaction time (h) | Yield (%) | syn/anti |
|---|---|---|---|---|
| 1 | $PhCO_2H$ | 24 | 90 | 92/8 |
| 2 | $CH_3CO_2H$ | 18 | 93 | 92/8 |
| 3 | HCl | 2 | 76 | 89/11 |
| 4 | TsOH | 2 | 69 | 89/11 |
| 5 | — | 24 | trace | — |

From Table 3, it was concluded that various Brønsted acids such as acetic acid, hydrochloric acid and p-toluenesulfonic acid accelerate the reaction and increase the syn selectivity.

Example 4

Aldol Reactions of Various Substrates and Stereoselectivities

Aldol reactions between various aldehydes and various silyl enol ethers were carried out using $Ph_2BOH$. The substrates, yields and the diastereoselectivities are shown in Table 4.

TABLE 4

| Reaction No. | Substrate | | | Yield (%) syn/anti |
|---|---|---|---|---|
| 1[b] | PhCHO | | $OSiMe_3$ (propenyl) | [e] 60 (96/4) |
| 2[b] | | | $OSiMe_3$ | [f] 72 (53/47) |
| 3[b] | | | $OSiMe_3$ | [g] 72 (95/5) |
| 4[b] | | | $OSiMe_3$, $Si^tBu$ | [h] 62 (96/4) |
| 5[b,c] | | | $OSiMe_3$, $S^tBu$ | [i] 84[k] (39/61) |
| 6[b] | 4-Cl-C$_6$H$_4$CHO | | $OSiMe_3$ | 51 (95/5) |
| 7 | 4-Cl-C$_6$H$_4$CHO | | $OSiMe_3$, Ph | [j] 92 (90/10) |
| 8[b] | 2-naphthyl-CHO | | $OSiMe_3$ | 74 (97/3) |
| 9 | 1-naphthyl-CHO | | $OSiMe_3$, Ph | 80 (92/8) |
| 10 | | | $OSiMe_3$ (cyclohexenyl) | 79 (47/53) |

TABLE 4-continued

| Reaction No. | Substrate | Yield (%) syn/anti |
|---|---|---|
| 11[d] | (structure: Ph-CH=CH-CHO and OSiMe3/Ph enolate) | 76 (91/9) |
| 12 | (structure: Ph-CH2-CH2-CHO) | 61 (92/8) |

(Conditions: [a]silyl enolate (1.5 eq.), Compound 1 (0.1 eq.), PhCO$_2$H (0.01 eq.), SDS (0.1 eq.), H$_2$O (aldehyde: 167 mM), 30° C., 4 to 24 hours; [b]silyl enolate (3.0 eq.); [c]0° C.; [d]PhCO$_2$H (0.1 eq.); [e]Z/E = >99/<1; [f]Z/E = 19/81; [g]Z/E = 96/4; [h]Z/E = 2/98; [i]Z/E = 97/3; [j]Z/E = >99/<1; [k]72 hours.)

In the presence of Ph$_2$BOH (0.1 equiv.), SDS (0.1 equiv.), and benzoic acid (0.01 equiv.), the reaction for all substrates proceeded to provide products in high yield.

The highest diastereoselectivities (syn/anti=96/4-97/3) were obtained in the system where (Z)-3-trimethylsiloxy-2-pentene was used (Reaction Nos. 1 and 8). Further, all reactions using Z-enolate led to high syn selectivity (syn/anti=90/10-97/3). Further, not only aromatic aldehydes but also α,β-unsaturated aldehydes exhibited high syn selectivity. When E-enolates were used as the substrate, the diastereoselectivity decreased (Reaction Nos. 2 and 10); however, when silyl enolates derived from tert-butyl thiopropionate were used (Reaction Nos. 4 and 5), reverse diastereoselectivity was observed.

Therefore, it is presumed that Ph$_2$BOH is acting as a Lewis acid catalyst in the present method for aldol reaction. However, because the present method exhibited diastereoselectivities much higher than those obtained by conventional Mukaiyama aldol reactions in water using Lewis acid catalysts, it was suggested that the reaction actually proceeded by a mechanism much different from that of conventional Lewis acid catalyst systems.

Reference Example 1

Reaction Mechanism for Aldol Reaction in Water Using Diphenylboronic Acid

To elucidate the mechanism for the aldol reaction in water between aldehyde and silyl enol ether in the presence of Ph$_2$BOH, benzaldehyde (PhCHO) and cyclohexane carboxyaldehyde (CyCHO) were used as the aldehyde and reacted with Compound 2 under the conditions shown in the following chemical formula (C).

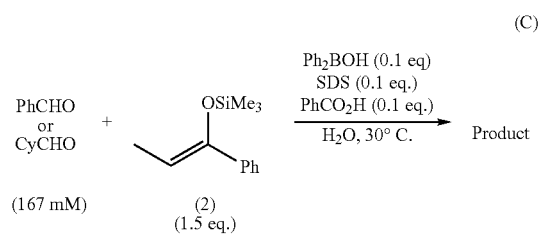

Here, the rate of disappearance of silyl enolate (Compound 2) was measured by HPLC (internal standard: acetophenone). The results are shown in FIG. 1.

As shown in FIG. 1a, the rate of disappearance of the silyl enolate was independent of the reactivities of the aldehydes, and remained approximately constant. Further, it was found that the silyl enolate disappeared at the same rate also for the system where Ph$_2$BOH, benzoic acid and SDS were added to an aqueous solution of the silyl enolate without the addition of an aldehyde.

Furthermore, it was apparent that the reaction was a first-order reaction (k=3.0×10$^{-4}$ [S$^{-1}$]), in which the reaction rate was dependent only on the concentration of the silyl enolate (FIG. 1b).

From these results, it was suggested that a boron enolate intermediate was generated from the reaction between Ph$_2$BOH and silyl enolate, and that the aldol reaction proceeded via this boron enolate intermediate, as shown in the following chemical formula (D).

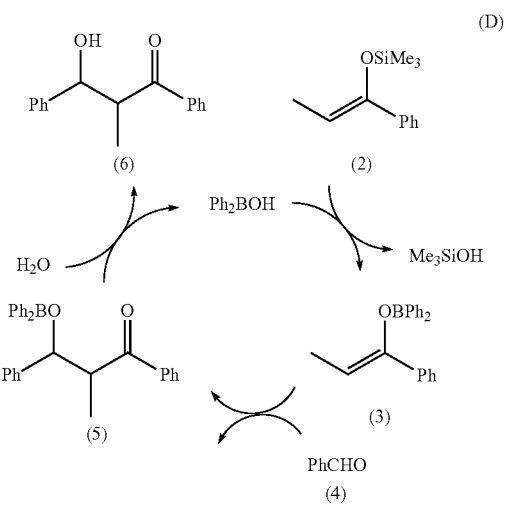

INDUSTRIAL APPLICABILITY

As described in detail above, a method for aldol reaction that gives products in high yield and stereoselectivity in water is provided by the present invention. In the method of the present invention, by using only a catalytic amount of the boron source, a boron enolate intermediate that is stable in water is generated, and the product is obtained in high yield and selectivity from aldehyde and silyl enolate. This method uses no organic solvent and thereby does not require drying of the reagents, etc., and is thus highly useful as a simple, environmentally-benign method.

The invention claimed is:

1. A method for aldol reaction in water, which comprises reacting an aldehyde with a silyl enol ether in an aqueous medium in the presence of a boronic acid represented by the following general formula (1):

$$R^1R^2BOH \quad (1)$$

(wherein $R^1$ and $R^2$ are the same or different hydrocarbon groups that may contain a substituent), a surfactant, and a Brønsted acid.

2. The method for aldol reaction in water of claim 1, wherein the surfactant is an anionic surfactant.

3. The method for aldol reaction in water of claim 1, wherein the Brønsted acid is an organic acid.

4. The method for aldol reaction in water of claim 1, wherein the boronic acid represented by the general formula (1):

$$R^1R^2BOH \qquad (1)$$

(wherein $R^1$ and $R^2$ are the same or different hydrocarbon groups that may contain a substituent) is bonded to a silyl enolate to form a boron enolate intermediate.

5. The method for aldol reaction in water of claim 2, wherein the Brønsted acid is an organic acid.

6. The method for aldol reaction in water of claim 2, wherein the boronic acid represented by the general formula (1):

$$R^1R^2BOH \qquad (1)$$

(wherein $R^1$ and $R^2$ are the same or different hydrocarbon groups that may contain a substituent) is bonded to a silyl enolate to form a boron enolate intermediate.

7. The method for aldol reaction in water of claim 3, wherein the boronic acid represented by the general formula (1):

$$R^1R^2BOH \qquad (1)$$

(wherein $R^1$ and $R^2$ are the same or different hydrocarbon groups that may contain a substituent) is bonded to a silyl enolate to form a boron enolate intermediate.

8. The method for aldol reaction in water of claim 4, wherein the boronic acid represented by the general formula (1):

$$R^1R^2BOH \qquad (1)$$

(wherein $R^1$ and $R^2$ are the same or different hydrocarbon groups that may contain a substituent) is bonded to a silyl enolate to form a boron enolate intermediate.

9. The method for aldol reaction in water of claim 5, wherein the boronic acid represented by the general formula (1):

$$R^1R^2BOH \qquad (1)$$

(wherein $R^1$ and $R^2$ are the same or different hydrocarbon groups that may contain a substituent) is bonded to a silyl enolate to form a boron enolate intermediate.

* * * * *